United States Patent
Kamitamari et al.

(10) Patent No.: US 7,009,079 B2
(45) Date of Patent: *Mar. 7, 2006

(54) CHIRAL COPPER COMPLEX AND PRODUCTION PROCESSES THEREOF AND USING THE SAME

(75) Inventors: Masashi Kamitamari, Toyonaka (JP); Gohfu Suzukamo, Suita (JP); Michio Yamamoto, Otsu (JP); Koji Hagiya, Takatsuki (JP); Makoto Itagaki, Takatsuki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 203 days.

This patent is subject to a terminal disclaimer.

(21) Appl. No.: 10/625,604

(22) Filed: Jul. 24, 2003

(65) Prior Publication Data

US 2005/0090684 A1    Apr. 28, 2005

Related U.S. Application Data

(62) Division of application No. 09/766,575, filed on Jan. 23, 2001, now Pat. No. 6,670,500.

(30) Foreign Application Priority Data

Jan. 25, 2000 (JP) .......................... 2000-016279
Jan. 25, 2000 (JP) .......................... 2000-016280
Jan. 27, 2000 (JP) .......................... 2000-018595

(51) Int. Cl.
    *C07C 251/24*    (2006.01)
(52) U.S. Cl. .................. 564/272; 564/273; 564/275; 568/704; 568/716; 560/124
(58) Field of Classification Search ............... 564/272, 564/273, 275; 560/124
    See application file for complete search history.

(56) References Cited

U.S. PATENT DOCUMENTS

| | | |
|---|---|---|
| 3,868,401 A | 2/1975 | Aratani et al. |
| 4,029,683 A | 6/1977 | Aratani et al. |
| 4,029,690 A | 6/1977 | Aratani et al. |
| 4,197,408 A | 4/1980 | Aratani et al. |
| 4,552,972 A | 11/1985 | Aratani et al. |
| 4,603,218 A | 7/1986 | Aratani et al. |
| 6,469,198 B1 * | 10/2002 | Suzukamo et al. ......... 560/124 |

FOREIGN PATENT DOCUMENTS

| | | |
|---|---|---|
| GB | 1075582 A | 7/1967 |
| GB | 1455189 A | 11/1976 |
| JP | 5473758 A | 6/1979 |

OTHER PUBLICATIONS

Zhengning Li et al.; Tetrahedron: Asymmetry 11 (Jan. 11, 2000) pp. 1157-1163.
Zhengning Li et al.; Tetrahedron 56 (Jul. 6, 2000) pp. 7187-7191.
Tadatoshi Aratani; Pure & Appl. Chem., vol. 57, No. 12 (1985) pp. 1839-1844.
H. Brunner et al., Journal of Organometallic Chemistry, vol. 501, No. 1, pp. 161-166 (Oct. 4, 1995), XP004023748.
D.A. Cogan et al., J. Am. Chem. Soc., vol. 120, No. 32, pp. 8011-8019 (Aug. 19, 1998).
J.J. Calienni et al., Inorg. Chim. ACTA, vol. 116, No. 2, pp. 163-169 (1986).
Database CAPLUS on STN, Acc. No. 1975:3854, Aratani, US 4,029,690 and US 4,029,683 (abstract).

* cited by examiner

*Primary Examiner*—Brian Davis
(74) *Attorney, Agent, or Firm*—Birch, Stewart, Kolasch & Birch, LLP

(57) ABSTRACT

There is disclosed an optically active salicylideneaminoalcohol compound of formula (1):

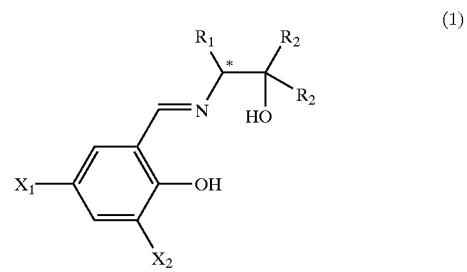

wherein $R_1$ represents an alkyl group or the like, $R_2$ represents
  an aryl group and the like, and
  when $X_1$ represents a nitro, $X_2$ is a hydrogen atom,
  when $X_1$ represents a chlorine atom, $X_2$ is a chlorine atom, and
  when $X_1$ is a hydrogen atom, $X_2$ is a fluorine atom; and
  the carbon atom denoted by "*" is an asymmetric carbon atom having either an S or R configuration, and a chiral copper complex produced from the optically active salicylidenaminoalcohol compound and a copper compound.

9 Claims, No Drawings

CHIRAL COPPER COMPLEX AND PRODUCTION PROCESSES THEREOF AND USING THE SAME

This application is a divisional of application Ser. No. 09/766,575, filed on Jan. 23, 2001 now U.S. Pat. No. 6,670,500, the entire contents of which are hereby incorporated by reference and for which priority is claimed under 35 U.S.C. § 120; and this application claims priority of Application Nos. 2000-016279, 2000-016280 and 2000-018595 filed in Japan on Jan. 25, 2000, Jan. 25, 2000 and Jan. 27, 2000, respectively under 35 U.S.C. § 119.

FIELD OF THE INVENTION

The present invention relates to a chiral copper complex, the production process thereof using chiral salicylidene ligands and asymmetric synthesis of cyclopropane-carboxylic acid compound using the complex as a catalyst.

BACKGROUND OF THE INVENTION

As a process for producing an optically active cyclopropanecarboxylic acid ester derivative, there have been known a process of reacting an olefin with a diazoacetic acid ester in the presence of a certain salicylideneaminoalcohol copper complex catalyst (JP-A 59-225194).

SUMMARY OF THE INVENTION

According to the present invention, an industrially suitable chiral copper complex comprising an optically active salicylidenaminoalcohol compound can be readily produced. Said complex is more stable to an oxide that can be contained in a cyclopropanation reaction system, reducing adverse effects of such an oxide and said salicylidenaminoalcohol compound can be recovered after said reaction in an improved yield, The present invention provides:

1. an optically active salicylideneaminoalcohol compound of formula (1):

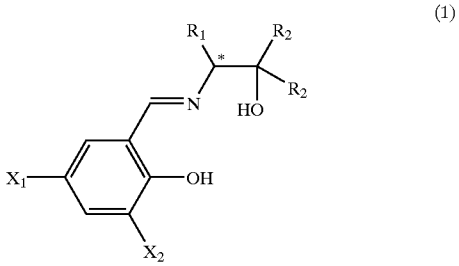

wherein $R_1$ represents
an alkyl group which may be substituted with a group selected from an alkoxy group, an aralkyloxy group, an aryloxy group and cycloalkoxy group,
an aralkyl, aryl or cycloalkyl group all of which may be substituted with a group selected from an alkyl group, an alkoxy group, an aralkyloxy group, an aryloxy group, and a cycloalkoxy group,
$R_2$ represents
an alkyl group, a cycloalkyl group, or
an aralkyl or phenyl group which may be substituted with a group selected from an alkyl group, an alkoxy group, an aralkyloxy group, an aryloxy group and a cycloalkoxy group, when $X_1$ represents a nitro, $X_2$ is a hydrogen atom,
when $X_1$ represents a chlorine atom, $X_2$ is a chlorine atom, and
when $X_1$ is a hydrogen atom, $X_2$ is a fluorine atom, and
the carbon atom denoted by "*" is an asymmetric carbon atom having either an S or R configuration, 2. a process for producing an optically active salicylideneaminoalcohol compound as defined above, which comprises reacting an optically active amino alcohol of formula (2):

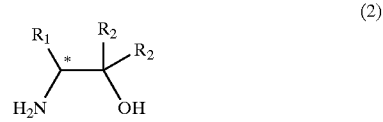

wherein $R_1$, $R_2$ and "*" have the same meaning s as defined above, with a 2-hydroxybenzaldehyde derivative of formula (3):

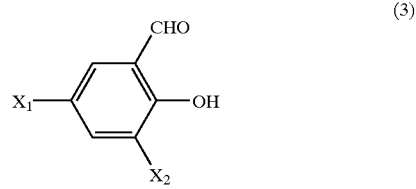

wherein when $X_1$ and $X_2$ are the same as defined above, 3. a chiral copper complex prepared from a mono-valent or di-valent copper compound and an optically active salicylideneaminoalcohol compound (1) as defined above, 4. a method for producing a chiral copper complex of formula (1):

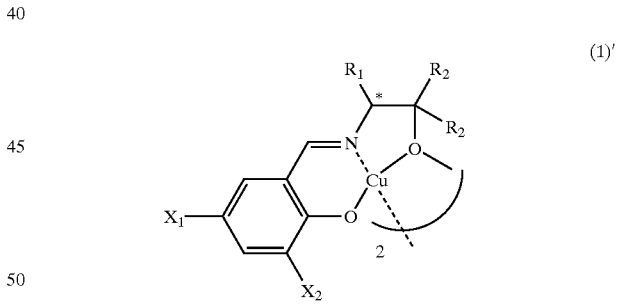

wherein $R_1$ and $R_2$ are the same or different and independently represent an alkyl group, an aralkyl group, a phenyl group, a 2-methoxyphenyl group, a 2-tert-butoxy-5-tert-butylphenyl group, or a 2-octyloxy-5-tert-butylphenyl group;
when $X_1$ represents a nitro group, $X_2$ is a hydrogen atom,
when $X_1$ represents a chlorine atom, $X_2$ is a chlorine atom, and
when $X_1$ represents a hydrogen atom, $X_2$ is a fluorine atom
the carbon atom denoted by "*" is an asymmetric carbon atom having either an S or R configuration,
which comprises contacting a di-valent copper compound, in an inert organic solvent, with a chiral salicylideneaminoalcohol compound of formula (1):

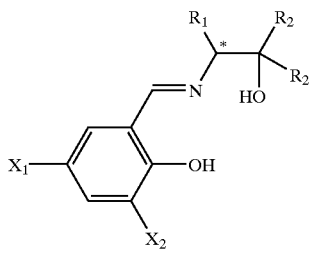

wherein $R_1$, $R_2X_1$, $X_2$ and "*" respectively have the same meaning as defined above, and 5. a method for producing an optically active cyclopropane-carboxylic acid ester of formula (4):

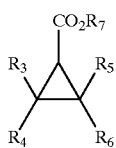

wherein $R_3$, $R_4$, $R_5$, $R_6$ and $R_7$ are as defined below,
which comprises reacting a prochiral olefin of formula (5):

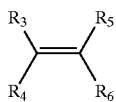

wherein $R_3$, $R_4$, $R_5$ and $R_6$ are as defined below, with a diazoacetic acid ester of formula (6):

wherein $R_7$ is as defined below, in the presence of a chiral copper complex as defined in item 3 or 4, wherein $R_3$, $R_4$, $R_5$ and $R_6$ independently represent
   a hydrogen atom,
   a halogen atom,
   a (C1–C8)alkyl group which may be substituted with a halogen atom or a lower alkoxy group,
   a (C4–C8)cycloalkyl group,
   an aryl group which may be substituted with a halogen atom or a lower alkoxy group,
   an alkoxy group,
   $R_3$ and $R_4$, or $R_5$ and $R_6$ may be bonded at their terminals to form an alkylene group having 2–4 carbon atoms, and
      one of $R_3$, $R_4$, $R_5$ and $R_6$ groups represents an alkenyl group which may be substituted with a halogen atom, an alkoxy group or an alkoxy carbonyl group, of which alkoxy may be substituted with a halogen atom or atoms,
   provided that when $R_3$ and $R_5$ are the same, $R_4$ and $R_6$ are not the same, and
   $R_7$ represents an alkyl group having 1 to 8 carbon atoms, a cycloalkyl group which may be optionally substituted with a lower alkyl group,
      a benzyl group which may be optionally substituted with a lower alkyl group, a lower alkoxy group, a phenoxy group or a halogen atom,
      a phenyl group which may be optionally substituted with a lower alkyl group, a lower alkoxy group or a phenoxy group,

DETAILED DESCRIPTION

First, a description will be made to the optically active salicylideneaminoalcohol compound of formula (1) as defined above.

Examples of the alkyl group which may be substituted with a group selected from an alkoxy group, an aralkyloxy group, an aryloxy group, and a cycloalkoxy group, represented by $R_1$, include
   a (C1–C8)alkyl group (e.g., a methyl, ethyl, n-propyl, i-propyl, n-butyl, i-butyl, sec-butyl, t-butyl, n-pentyl, n-hexyl, n-pentyl, n-octyl, n-nonyl, or n-decyl group) which may be substituted with a group selected from a (C1–C4) alkoxy group(e.g., a methoxy, ethoxy, n-propoxy, i-propoxy, n-butoxy, i-butoxy, sec-butoxy, or t-butoxy group),
   a (C7–C11)aralkyloxy group(e.g., a benzyloxy, or naphthylmethyloxy group),
   a (C6–C11)aryloxy group(e.g., a phenoxy, or naphthoxy group) and
   a (C4–C6)cycloalkoxy group(e.g., cyclobutyloxy, cyclopentyloxy, cyclohexyloxy group).

Examples of the aralkyl group, the aryl group, and the cycloalkyl group, all of which may be substituted with a group selected from an alkyl group, an alkoxy group, an aralkyloxy group, an aryloxy group, and a cycloalkoxy group include
   a (C7–C11)aralkyl group(e.g., a benzyl, or naphthylmethyl group),
   a (C6–C10)aryl group(e.g., a phenyl, or naphthyl group,
   a (C4–C6)cycloalkyl group(e.g., a cyclobutyl, cyclopentyl, or cyclohexyl group), all of which may be substituted with a group as specified above.

The alkyl group represented by $R_2$ has the same meanings as defined above for the (C1–C8)alkyl group, The cycloalkyl group, and the aralkyl or phenyl group which may be substituted with a group selected from an alkyl group, an alkoxy group, an aralkyloxy group, an aryloxy group and a cycloalkoxy group represented by $R_2$ have the same meanings as defined above for $R_1$.

Among the optically active salicylideneaminoalcohol compound of formula (1), $R_1$ and $R_2$ are preferably an alkyl group (e.g. lower alkyl groups having 1 to 4 carbon atoms such as methyl group, ethyl group, n-propyl group, isopropyl group, n-butyl group, tertbutyl group or the like), an aralkyl group (e.g., a benzyl group), an aryl group (e.g., a phenyl group, a 2-methoxyphenyl group, a 2-tert-butoxy-5-tert-butylphenyl group or a 2-octyloxy-5-tert-butylphenyl group).

Specific examples the optically active salicylideneaminoalcohol compound of formula (1) include optically active
N-(3-fluorosalicyliden)-2-amino-1,1-di(2-butoxy-5-t-butylphenyl)-1-propanol,
N-(3-fluorosalicyliden)-2-amino-1,1-di(2-octyloxy-5-t-butylphenyl)-1-propanol,
N-(3-fluorosalicyliden)-2-amino-1,1-di(2-butoxy-5-t-butylphenyl)-3-phenyl-1-propanol,
N-(3-fluorosalicyliden)-2-amino-1,1-di(2-methoxyphenyl)-1-propanol,
N-(3-fluorosalicyliden)-2-amino-1,1-diphenyl-1-propanol,
N-(3-fluorosalicyliden)-2-amino-1,1-di(2-benzyloxy-5-methylphenyl)-3-(4-isopropoxyphenyl)-1-propanol, N-(3-fluorosalicyliden)-2-amino-1,1-diphenyl-3-phenyl-1-propanol,
N-(3-fluorosalicyliden)-2-amino-1,1-di(2-methoxyphenyl)-3-methyl-1-butanol,
N-(3,5-dichlorosalicylidene)-2-amino-1,1-diphenyl-1-propanol,
N-(3,5-dichlorosahicylidene)-2-amino-1,1-di-(2-methoxyphenyl)-1-propanol
N-(3,5-dichlorosalicylidene)-2-amino-1,1-di(5-tert-butyl-2-tert-butoxyphenyl)-3-phenyl-1-propanol,
N-(3,5-dichlorosalicylidene)-2-amino-1,1-di-(5-tert-butyl-2-octyloxyphenyl)-1-propanol
N-(3,5-dichlorosalicylidene)-2-amino-1,1-di(2-methoxyphenyl)-3-methyl-1-butanol,
N-(5-nitrosalicyliden)-2-amino-1,1-diphenyl-1-propanol,
N-(5-nitrosalicyliden)-2-amino-1,1-diphenyl-3-phenyl-1-propanol,
N-(5-nitrosalicyliden)-2-amino-1,1-di(2-butoxy-5-t-butylphenyl)-3-phenyl-1-propanol,
N-(5-nitrosalicyliden)-2-amino-1,1-di(2-benzyloxy-5-methylphenyl)-3-(4-isopropoxyphenyl)-1-propanol,
N-(5-nitrosalicyliden)-2-amino-1,1-di(2-methoxyphenyl)-1-propanol,
N-(5-nitrosalicyliden)-2-amino-1,1-di(2-t-butyl-4-methylphenyl)-3-phenyl-1-propanol,
N-(5-nitrosaiicyliden)-2-amino-1,1-di(4-t-butylphenyl)-1-propanol,
N-(5-nitrosalicyliden)-2-amino-1,1-di(2-methoxyphenyl)-3-methyl-1-propanol,
N-(5-nitrosalicylidene)-2-amino-1,1-di-(5-tert-butyl-2-octyoxyphenl)-1-propanol,
N-(5-nitrosalicylidene)-2-amino-1,1-di(5-tert-butyl-2-tert-butoxyphenyl)-3-phenyl- 1-propanol,
N-(5-nitrosalicylidene)-2-amino-1,1-di(5-tert-butyl-2-tert-butoxyphenyl)-3-methyl-1-butanol and the like. Said optically active compounds have either an S configuration or R configuration with respect to the carbon atom denoted by "*" in the formula above.

Next, a description will be made to the process for producing the optically active salicylideneaminoalcohol compound of formula (1) comprising reacting an optically active amino alcohol of formula (2) with a salicylaldehyde derivative of formula (3) as defined above.

The optically active amino alcohol compound of formula (2) to be used in this process include those having $R_1$ and $R_2$ groups as specified above and specific examples thereof include optically active
2-amino-1,1-diphenyl-1-propanol,
2-amino-1,1-di(2-methoxyphenyl)-1-propanol,
2-amino-1,1-di(2-isopropoxyphenyl)-1-propanol,
2-amino-1,1-di(2-butoxy-5-t-butylphenyl)-1-propanol,
2-amino-1,1-diphenyl-3-phenyl-1-propanol,
2-amino-1,1-di(2-methoxyphenyl)-3-phenyl-1-propanol,
2-amino-1,1-di(2-isopropoxyphenyl)-3-phenyl-1-propanol,
2-amino-1,1-di(2-butoxy-5-t-butylphenyl)-3-phenyl-1-propanol,
2-amino-1,1-di(2-methoxyphenyl)-3-phenyl-1-butanol,
2-amino-1,1-di(2-butoxy-5-t-butylphenyl)-1-propanol,
2-amino-1,1-di(2-octyloxy-5-t-butylphenyl)-1-propanol,
2-amino-1,1-di(2-butoxy-5-t-butylphenyl-3-phenyl-1-propanol,
2-amino-1,1-di(2-methoxyphenyl)-1-propanol,
2-amino-1,1-di(2-benzyloxy-5-methylphenyl)-3-(4-isopropoxyphenyl)-1-propanol,
2-amino-1,1-di(2-methoxyphenyl)-3-methyl-1-butanol,
2-amino-1,1-di(2-t-butyl-4-methylphenyl)-3-phenyl-1-propanol,
2-amino-1,1-di(4-t-butylphenyl)-1-propanol,
2-amino-1,1-di(2-methoxyphenyl)-3-methyl-1-propanol
and the like.

The reaction of the optically active amino alcohol (2) with the salicylaldehyde derivative (3) is usually conducted at 20 to 150° C., preferably 50 to 120° C.

Said reaction is usually conducted by contacting the optically active amino alcohol with the slicylaldehyde derivative (3) in an organic solvent, examples of which include
an aromatic hydrocarbon solvent such as toluene, xylene or the like,
a halogenated hydrocarbon solvent such as chlorobenzene, dichloromethane, dichloroethane or the like,
an alcohol solvent such as methanol or the like,
an aliphatic hydrocarbon such as hexane, heptane, cyclohexane or the like,
an ether such as diethylether, methyl-t-butylether or the like, an ester such as methyl acetate, ethyl acetate or the like, and a mixture thereof. An amount thereof to be used is not particularly limited, An amount of the slicylaldehyde derivative to be used is usually 1 to 2 moles, preferably 1 to 1.5 moles per mol of the optically active amino alcohol of formula (2).

The salicylideneaminoalcohol of formula (1) is usually contacted with a mon-valent or di-valent copper compound to produce a chiral copper complex in a solvent.

Examples of the mono-valent or di-valent copper compound include
a copper salt of an organic carboxylic acid having 2 to 15 carbon atoms such as copper acetate, copper naphthenate, copper octanoate and the like, and
a copper salt such as copper chloride, copper bromide, copper nitrate, copper sulfate, copper methanesulfonte, copper trifluoromethanesulfonate, copper cyanate, or copper carbonate, and copper oxide, and a mixture thereof.

Examples of the solvent include a halogenated hydrocarbon such as dichloromethane, dichloroethane, chloroform, carbon tetrachloride or the like, and an aromatic hydrocarbon such as toluene, xylene or the like, an ether such as diethylether, methyl-t-butylether or the like, an ester such as methyl acetate, ethyl acetate or the like, and a mixture thereof. An amount thereof to be used is not particularly limited and is usually 2 to 500 parts by weight per 1 part by weight of the copper compound. Prochiral olefins of formula (6) to be used in the next cyclopropanation step may also be used as a solvent.

An amount of the optically active salicylideneaminoalcohol compound of formula (1) to be used is usually 0.5 to 5 moles, preferably 0.8 to 2.5 moles per mol of the copper compound. The reaction temperature is usually 10 to 120° C., preferably 20 to 100° C.

After completion of the reaction, the resulting reaction mixture containing the desired chiral copper complex may be used as it is in a solution form in the subsequent cyclopropanation reaction, or it may be washed with an aqueous alkali solution (e.g, aqueous solution of sodium hydrogencarbonate, sodium hydroxide, potassium hydroxide, sodium carbonate, potassium carbonate or the like) and the evaporated to give the desired chiral copper complex.

Alternatively the desired copper complex can be precipitated as a green colored crystal by cooling the reaction solution at a temperature of ranging from −50 to +30° C., preferably −10 to 20° C.

The copper complex may be also precipitated from the reaction solution by the addition of an aliphatic hydrocarbon solvent (e.g., hexane or heptane). The amount of the solvent to be used is 0.05 to 50 parts by weight, preferably 0.5 to 500 parts by weight per 1 part by weight of the solvent used for the preparation of the complex as above. After the addition of the solvent, the resulting mixture may be cooled thereafter to a temperature of 0 to 30° C.

Said precipitated crystals of the chiral copper complex can be separated by filtration from the reaction mixture, and collected crystals may be further washed with said aliphatic or aromatic hydrocarbon solvent (e.g., an aromatic or aliphatic hydrocarbon solvent such as toluene, hexane, heptane or the like), if necessary. The separated crystal can be subjected to high-performance liquid chromatography or elemental analysis to calculate the yield or purity thereof.

The chiral copper complex can form an adduct with a prochiral olefin of formula (5). Said adduct can be obtained by contacting the isolated chiral copper complex with the prochiral olefin of formula (5) or by using the prochiral olefin as a solvent to produce the chiral copper complex. The adduct can be used as a catalyst in the cyclopropanation reaction.

The chiral copper complex having an optically active salicylideneaminoalcohol compound of formula (1) wherein $R_1$ and $R_2$ are the same or different and independently represent an alkyl group, an aralkyl group, a phenyl group, a 2-methoxyphenyl group, a 2-tert-butoxy-5-tert-butylphenyl group or a 2-octyloxy-5-tert-butylphenyl group, and $X_1$ represents a nitro group and $X_2$ is a hydrogen atom, $X_1$ represents a chlorine atom and $X_2$ is a chlorine atom, or $X_1$ represents a hydrogen atom and $X_2$ is a fluorine atom as shown by formula (1)' above can be obtained in a crystal form.

A description will be made to the process for producing optically active cyclopropanecarboxylic acid ester of formula (4) as defined above comprising reacting a prochiral olefin of formula (5) with a diazoacetic acid ester of formula (6) in the presence of a chiral copper complex thus obtained.

Examples of the alkoxy group represented by $R_3$, $R_4$, $R_5$ or $R_6$ of the prochiral olefin include an alkoxy group having 1 to 3 carbon atoms such as a methoxy, ethoxy, n-propoxy, i-propoxy, or the like.

Examples of the alkyl group which may be substituted with a halogen atom or an alkoxy group include a linear or branched alkyl group having 1 to 10 carbon atoms such as a methyl, ethyl, n-propyl, isopropyl, n-butyl, isobutyl, sec-butyl, tert-butyl, n-pentyl, n-hexyl, n-heptyl, n-octyl, n-nonyl, or n-decyl group, an alkyl group substituted with a halogen atom such as a fluorine atom, a chlorine atom, a bromine atom and the like a haloalkyl group such as a chloromethyl, dichloromethyl, trichloromethyl, difluoromethyl, trifluoromethyl, 2,2,2-trichloroethyl group or the like), an alkyl group substituted with an alkoxy group such as a methoxy, ethoxy, n-propoxy, i-propoxy group or the like.

Examples of the alkylene group formed by $R_2$ and $R_4$, or $R_5$ and $R_6$ include an alkylene group having 2 to 4 carbon atoms such as dimethylnene, trimethylene, or tetramethylene group.

Examples of the alkenyl group which may be substituted with a halogen atom, an alkoxy group or an alkoxy carbonyl group, of which alkoxy may be substituted with a halogen atom or atoms, represented by $R_3$, $R_4$, $R_5$ include a linear or branched alkenyl groups having 1 to 10 carbon atoms such as an ethenyl, propenyl, 2-methylpropenyl, 1-butenyl, 2-butenyl, or hexenyl group, a haloalkenyl group, which is the above-described alkenyl group substituted with the above-described halogen atom or atoms, such as a chloroethenyl group, a chloropropenyl group, 2,2-dichloroethenyl group, 2,2-difluoroethenyl group or the like, an alkoxy(C1–C3)carbonyl substituted alkenyl group such as
2-methoxycarbonyl-2-methylethenyl group,
2-ethoxycarbonyl-2-methylethenyl group,
2-(1,1,1,3,3,3-hexafluoroisopropoxycarbonyl)-1-methylethenyl group or the like.

Specific examples of the prochiral olefin (5) include propene, 1-butene, isobutylene, 1-pentene, 1-hexene, 1-octene,
4-chloro-1-butene, 1-chloro-2-methylpropene, 2-pentene, 2-heptene,
2-methyl-2-butene, 2,5-dimethyl-2,4-hexadiene,
2-chloro-5-methyl-2,4-hexadiene, 2-fluoro-5-methyl-2,4-hexadiene,
1,1,1-trifluoro-5-methyl-2,4-hexadiene,
1,1,1-trifluoro-2-chloro-5-methyl-2,4-hexadiene,
2-methoxycarbonyl-5-methyl-2,4-hexadiene,
2-ethoxycarbonyl-5-methyl-2,4-hexadiene,
1,1-difluoro-4-methyl-1,3-pentadiene, 1,1-dichloro-4-methyl-1,3-pentadiene,
1,1-dichloro-2,4-dimethyl-1,3-pentadiene, 2-methyl-2,4-hexadiene,
2,3-dimethyl-2-pentene, 1,1,1-trichloro-4-methyl-3-pentene and the like.
1,1-dibromo-4-methyl-1,3-pentadiene,
1-chloro-1-fluoro-4-methyl-1,3-pentadiene,
1-chloro-1-(4-chlorophenyl)-4-methyl-1,3-pentadiene,
1-fluoro-1-bromo-4-methyl-1,3-pentadiene,
2-(1,1,1,3,3,3-hexafluoroisopropoxycarbonyl)-5-methyl-2,4-hexadiene,
1-methoxy-4-methyl-1,3-pentadiene,
1-ethoxy-4-methyl-1,3-pentadiene,
1-propoxy-4-methyl-1,3-pentadiene,
1-fluoro-1-methoxy-4-methyl-1,3-pentadiene,
1-fluoro-1-ethoxy-4-methyl-1,3-pentadiene,
1-fluoro-1-propoxy-4-methyl-1,3-pentadiene,
1,1,1-tribromo-4-methyl-3-pentene, 2-bromo-2,2-dimethyl-4-hexene,
2-chloro-2,5-dimethyl-4-hexene, 1-methoxy-2-methyl-1-propene,
1-ethoxy-2-methyl-1-propene, 1-propoxy-2-methyl-1-propene,
1-methoxy-8-methyl-2-butene, 1-ethoxy-3-methyl-2-butene,
1-propoxy-3-methyl-2-butene, 1,1-dimethoxy-3-methyl-2-butene,
1,1-diethoxy-3-methyl-2-butene, isopropylidenecyclopropane,
isopropylidenecyclobutane, 2-methyl-4-cyclopenthylidene-2-buten,
isopropylidenecyclopentane and the like.

Preferably, $R_3$ and $R_4$, or $R_5$ and $R_6$ represent a methyl group. More preferred prochiral olefins are isobutylexne and 2,5-dimethyl-2,4-hexadiene.

Examples of the alkyl group having 1 to 8 carbon atoms represented by $R_7$ in the diazoacetic acid ester of formula (6) include a methyl group, an ethyl group, a n-propyl group, an isopropyl group, a n-butyl group, an isobutyl group, a sec-butyl group, a tert-butyl group, a n-pentyl group, a n-hexyl group, a n-octyl group and the like.

Examples of the cycloalkyl group which may be optionally substituted with a lower alkyl group include a cyclohexyl group, a l-menthyl group, a d-menthyl group, an adamantyl group.

Examples of the phenyl group which may be optionally substituted with a lower alkyl group, a lower alkoxy group or a phenoxy group represented by $R_7$ in formula (6) include a phenyl group, 2-methylphenyl group, 3,5-dimethylphenyl group, 4-methyl-2,6-di-tert-butylphenyl group, 2-methoxyphenyl group, 3,5-dimethoxyphenyl group and the like.

Examples of the benzyl group which may be optionally substituted with a lower alkyl group, a lower alkoxy group, a phenoxy group or a halogen atom, represented by $R_7$ in formula (6) include a 3-phenoxybenzyl group, 2-methyl-3-phenylbenzyl group, 2,3,5,6-tetrafluorobenzyl group, 2,3,5,6-tetrafluoro-4-methylbenzyl group and the like.

Examples of the lower alkyl group which may be present on the cycloalkyl group or on the phenyl group include a (C1–C4)alkyl group such as a methyl group, an ethyl group, a n-propyl group, an i-propyl group, a n-butyl group, an i-butyl group, a sec-butyl group, and a t-butyl group.

Examples of the lower alkoxy group which may be present on the phenyl group include a (C1–C4)alkoxyl group such as a methoxy group, an ethoxy group, a n-propoxy group, an i-propoxy group, a n-butoxy group, an i-butoxy group, a sec-butoxy group, and a t-butoxy group.

Preferred are a (C1–C6)alkyl group, a phenyl group which may be optionally substituted with a lower alkyl group, a lower alkoxy group or a phenoxy group such as a phenyl group, 2-methylphenyl group, 3,5-dimethylphenyl group, 4-methyl-2,6-di-tert-butylphenyl group, 2-methoxyphenyl group, 3,5-dimethoxyphenyl group, a cyclohexyl group, a 1-menthyl group, a d-menthyl group, and 2,3,6,6-tetrafluorobenzyl group and 3-phenoxybenzyl group.

Specific examples of the diazoacetic acid ester of formula (6) include ethyl diazoacetate, n-propyl diazoacetate, tert-butyl diazoacetate, phenyl diazoacetate, 1-menthyl diazoacetate, 4-methyl-2,6-di-tert-butylphenyl diazoacetate,2,3,5,6-tetrafluorobenzyl diazoacetate, 3-phenoxybenzyl diazoacetate and the like.

Said diazoacetic esters of formula (6) is commercially available or may be prepared by the known method such as a method of reacting corresponding amino acid esters with a diazotizing agent prepared from sodium nitrite and mineral acids may be used.

The reaction of prochiral olefin of formula (5) with diazoacetic esters of formula (6) in the presence of the prepared chiral copper complex catalyst is usually performed by adding the diazoacetic ester of formula (6) to a mixture of the copper complex catalyst and the prochiral olefin of (5) and optionally in a solvent. As described above, the present reaction may be performed in the presence of a reducing agent such as phenylhydrazine or the like.

An amount of prochiral olefin of formula (5) to be used is usually 1 or mole or more per mol of the diazoacetic acid ester of formula (6). The upper limit thereof is not particularly limited and, for example, a large excess amount may be used so as to serve as a reaction solvent.

An amount of the copper complex catalyst to be used is usually 0.001 to 5 mole %, preferably 0.03 to 1 mole % in terms of copper relative to the diazoacetic ester of formula (6).

Examples of the solvent to be used include a halogenated hydrocarbon such as 1,2-dihloroethane, chloroform, carbon tetrachloride or the like, an aliphatic hydrocarbon such as hexane, heptane, cyclohexane and the like, an aromatic hydrocarbon such as benzene, toluene, xylene and the like, an ester such as methyl acetate, ethyl acetate and the like, and a mixture thereof. Alternatively, the prochiral olefin (5) may be used as a solvent.

An amount of a solvent to be used is usually 2 to 50 parts by weight, preferably 3 to 30 parts by weight per 1 part by weight of the diazoacetic ester (6).

A reaction temperature is usually −20 to 150° C., preferably −10 to 120° C. In addition, the reaction is usually performed under an inert gas 35 atmosphere such as a nitrogen gas or the like and the inert gas may contain, for example, 5% or less oxygen gas. In addition, the reaction can be conducted in the presence of excess amount of peroxide, for example, 20 moles or less, preferably 10 moles or less of peroxide per mol of the copper complex in the reaction without accompanying substantial adverse effect.

After completion of the reaction, the optically active cyclopropanecarboxylic acid ester derivative of formula (4) can be separated by distillation or the like, which may be further subjected to ester hydrolysis or the like, or may be further purified, for example, by distillation, column chromatography or the like, if necessary.

Examples of the optically active cyclopropanecarboxylic acid esters of formula (4) include optically active
methyl 2-methylcyclopropanecarboxylate,
ethyl 2-methylcyclopropanecarboxylate,
n-propyl 2-methylcyclopropanecarboxylate,
isopropyl 2-methylcyclopropanecarboxylate,
isobutyl 2-methylcyclopropanecarboxylate,
tert-butyl 2-methylcyclopropanecarboxylate,
cyclohexyl 2-methylcyclopropanecarboxylate,
menthyl 2-methylcyclopropanecarboxylate,
(4-methyl-2,6-di-tert-butylphenyl)2methylcyclopropanecarboxylate,
methyl 2,2-dimethylcyclopropanecarboxylate,
ethyl 2,2-dimethylcyclopropanecarboxylate,
n-propyl 2,2-dimethylcyclopropanecarboxylate,
isopropyl 2,2-dimethylcyclopropanecarboxylate,
isobutyl 2,2-dimethylcyclopropaanecarboxylate,
tert-butyl 2,2-dimethylcyclopropanecarboxylate,
cyclohexyl, 2,2dimethylcyclopropanecarboxylate,
menthyl 2,2-dimethylcyclopropanecarboxylate,
(4-methyl-2,6-di-tert-butylphenyl)2,2-dimethylcyclopropanecarboxylate,
methyl 2,2-dimethyl-3-(2-methyl-1-propenyl)cyclopropanecarboxylate,
ethyl 2,2-dimethyl-3-(2-methyl-1-propenyl)cyclopropanecarboxylate,
n-propyl 2,2-dimethyl-3-(2-methyl-1-propenyl)cyclopropanecarboxylate,
isopropyl 2,2-dimethyl-3-(2-methyl-1-propenyl)cyclopropanecarboxylate,
isobutyl 2,2-dimetyl-3-(3-methyl-1-propenyl)cyclopropanecarboxylate,
tert-butyl 2,2-dimethyl-3-(2-methyl-1-propenyl)cyclopropanecarboxylate,
cyclohexyl 2,2-dimethyl-3-(2-methyl-1-propenyl)cyclopropanecarboxylate,
menthyl 2,2-dimethyl-3-(2-methyl-1-propenyl)cyclopropanecarboxylate,
(4-methyl-2,6-di-tert-butylphenyl) 2,2-dimethyl-3-(2-methyl-1-propenyl)cyclopropanecarboxylate,
(3-phenoxybenzyl)2,2-dimethyl-3-(2-methyl-1-propenyl) cyclopropanecarboxylate,
(2,3,5,6-tetrafluoro-4-methoxymethylbenzyl)2,2-dimethyl-3-(2-methyl-1-propenyl)cyclopropanecarboxylate,
methyl 2,2-dimethyl-3(2,2-dichloro-1-ethenyl)cyclopropanecarboxylate,
ethyl 2,2-dimethyl-3-(2,2-dichloro-1-ethenyl)cyclopropanecarboxylate,
n-propyl 2,2-dimethyl-3-(2,2-dichloro-1-ethenyl)cyclopropanecarboxylate,
isopropyl 2,2-dimethyl-3-(2,2-dichloro-1-ethenyl)cyclopropanecarboxylate,
isobutyl 2,2-dimethyl-3-(2,2-dichloro-1-ethenyl)cyclopropanecarboxylate, tert-butyl 2,2-dimethyl-3-(2,2-dichloro-1-ethenyl)cyclopropanecarboxylate,
cyclohexyl 2,2-dimethyl-3-(2,2-dichloro-1-ethenyl)cyclopropanecarboxylate,
menthyl 2,2-dimethyl-3-(2,2-dichloro-1-ethenyl)cyclopropanecarboxylate,
(4-methyl-2,6-di-tert-butylphenyl)2,2-dimethyl-3-(2,2-dichloro-1-ethenyl)cyclopropanecarboxylate,
(3-phenoxybenzyl)2,2-dimethyl-3-(2,2-dichloro-1-ethenyl)cyclopropanecarboxylate,
(2,3,5,6-tetrafluoro-4-methoxymethylbenzyl)2,2-dimethyl-3-(2,2-dichloro-1-ethenyl)cyclopropanecarboxylate,
ethyl 2,2-dimethyl-3-(2,2-dibromo-1-ethenyl)cyclopropanecarboxylate,
methyl 2,2-dimethyl-3-(2,2,2-trichloroethyl)cyclopropanecarboxylate,
ethyl 2,2-dimethyl-3-(2,2,2-trichloroethyl)cyclopropanecarboxylate,
n-propyl 2,2-dimethyl-3-(2,2,2-trichloroethyl)cyclopropanecarboxylate,
isopropyl 2,2-dimethyl-3-(2,2,2-trichloroethyl)cyclopropanecarboxylate,
isobutyl 2,2-dimethyl-3-(2,2,2-trichloroethyl)cyclopropanecarboxylate,
tert-butyl 2,2-dimethyl-3-(2,2,2-trichloroethyl)cyclopropanecarboxylate,
cyclohexyl 2,2-dimethyl-3-(2,2,2-trichloroethyl)cyclopropanecarboxylate,
menthyl 2,2-dimethyl-3-(2,2,2-trichloroethyl)cyclopropanecarboxylate,
(4-methyl-2,6-di-tert-butylphenyl)2,2-dimethyl-3-(2,2,2-trichloroethyl)cyclopropanecarboxylate
(3-phenoxybenzyl)2,2-dimethyl-3-(2,2,2-trichloroethyl)cyclopropanecarboxylate,
(2,3,5,6-tetrafluoro-4-methoxymethylbenzyl)2,2-dimethyl-3-(2,2,2-trichloroethyl)cyclopropanecarboxylate,
methyl 2,2-dimethyl-3-(2-carboethoxy-1-propenyl)cyclopropanecarboxylate,
ethyl 2,2-dimethyl-3-(2-carbomethoxy-1-propenyl)cyclopropanecarboxylate,
n-propyl 2,2-dimethyl-3-(2-carboethoxy-1-propenyl)cyclopropanecarboxylate,
isopropyl 2,2-dimethyl-3-(2-carbomethoxy-1-propenyl)cyclopropanecarboxylate,
isobutyl 2,2-dimethyl-3-(2-carboethoxy-1-propenyl)cyclopropanecarboxylate,
tert-butyl 2,2-dimethyl-3-(2-carbomethoxy-1-propenyl)cyclopropanecarboxylate,
cyclohexyl 2,2-dimethyl-3-(2-carboethoxy-1-propenyl)cyclopropanecarboxylate,
menthyl 2,2-dimethyl-3-(2-carbomethoxy-1-propenyl)cyclopropanecarboxylate,
4-methyl-2,6-di-tert-butylphenyl 2,2-dimethyl-3-(2-carboethoxy-1-propenyl)cyclopropanecarboxylate
(3-phenoxybenzyl)2,2-dimethyl-3-(2-carbomethoxy-1-propenyl)cyclopropanecarboxylate,
(2,3,5,6-tetrafluoro-4-methoxymethylbenzyl)2,2-dimethyl-3-(2-carboethoxy-1-propenyl)cyclopropane-carboxylate,
ethyl 2,2-dimethyl-3-(2-chloro-2-(4-chlorophenyl)-1-ethenyl)cyclopropanecarboxylate,
ethyl 2,2-dimethyl-3-(2-chloro-2-trifluoromethyl-1-ethenyl)cyclopropanecarboxylate and the like.

The optically active salicylideneaminoalcohol compound of formula (1) contained in the residue after isolating the optically active cyclopropanecarboxylic acid ester derivative of formula (4) can be recovered by subjecting the residue to crystallization treatment, column chromatography or the like.

EXAMPLES

The present invention will be illustrated by way of the following Examples but are not to be construed to limit the present invention thereto.

Example 1

1.60 g of (R)-2-amino-1,1-di(2-methoxyphenyl)-1-propanol, 0.98 g of 2-hydroxy-5-nitrobenzaldehyde and 30 ml of toluene were mixed under a nitrogen atmosphere, and the mixture was stirred at 80° C. for 1 hour. Thereafter, toluene was distilled off, followed by crystallization to obtain 1.35 g of (R)-N-(5-nitrosalicylidene)-2-amino-1,1-(2-methoxyphenyl)-1-propanol.
Yield 74%
$^1$H-NMR (CDCl$_3$, TMS, ppm) δ: 1.41 (d, 3H, J=6.6 Hz), 3.62 (s, 6H), 5.26 (s, 1H), 5.66 (s, 1H), 6.65–7.27 (m, 8H), 7.52–7.67 (m, 2H), 8.03–8.10 (m, 3H)

Example 2

66.12 g of 2,5-dimethyl-2,4-hexadiene and 4 μg of phenylhydrazine were added to a 100 ml Schlenk tube purged with nitrogen, to which were dropwise added a toluene solution of a copper complex prepared from 3.59 mg of copper acetate monohydrate and 17.46 mg of (R)-N-(5-nitrosalicylidene)-2-amino-1,1-di(2-methoxyphenyl)-1-propanol, and a 9.9 g of a 2,5-dimethyl-2,4-hexadiene solution containing 2.28 g of ethyl diazoacetate over 2 hours at 80° C., respectively. Then, the mixture was stirred at the same temperature for 30 minutes. Gas chromatography analysis of the resulting reaction mixture showed that the yield of ethyl 2,2-dimethyl-3-(2-methyl-1-propenyl)cyclopropanecarboxylate was 97.4% and a trans/cis ratio was 59/41. It was shown by liquid chromatography analysis that optical purity of a (+)-trans-isomer was 56% ee and (+)-cis-isomer was 50% ee.

The reaction mixture was concentrated under reduced pressure to give a residue, which was analyzed by liquid chromatography. The recovery rate of the N-(5-nitrosalicylidene)-2-amino-1,1-di(2-methoxyphenyl)-1-propanol remaining in the residue was 22% (relative to employed (R)-N-(5-nitrosalicylidene)-2-amino-1,1-di(2-methoxyphenyl)-1-propanol).

Comparative Example 1

Ethyl 2,2-dimethyl-3-(2-methyl-1-propenyl)cyclopropanecarboxylate was produced in 96.2% according to a similar manner as in Example 2 except that 14.60 mg of (R)-N-salicyliden-2-amino-1,1-di(2-methoxyphenyl)-1-propanol was used instead of 17.46 mg of (R)-N-(5-nitrosalicylidene)-2-amino-1,1-di(2-methoxyphenyl)-1-propanol. A trans/cis ratio was 60/40. The optical purity of a (+)-trans-isomer was 35% ee and the optical puity of a (+)-cis-isomer was 36% ee.

In addition, the recovery rate of the N-salicyliden-2-amino-1,1-di(2-methoxyphenyl)-1-propanol was 5% (relative to the employed N-salicyliden-2-amino-1,1-di(2-methoxyphenyl)-1-propanol).

Example 3

2.00 g of (R)-N-(3,5-dichlorosalicylidene)-2-amino-1,1-di(2-methoxyphenyl)-1-propanol was obtained by a similar manner as in Example 1 except that 1.12 g of 2-hydroxy-3,5-dichlorobenzaldehyde was used instead of 0.98 g of 2-hydroxy-5-nitrobenzaldehyde. Yield 78%

$^1$H-NMR (CDCl$_3$, TMS, ppm) δ: 1.35 (d, 3H, J=6.61 Hz), 3.56 (d, 6H), 5.14 (q, 1H), 5.54 (s, 1H), 6.71–7.28 (m, 9H), 7.50–7.69 (m, 2H), 7.98 (s, 1H)

Example 4

2.0 g of (R)-2-amino-1,1-diphenyl-1-propanol, 1.47 g of 2-hydroxy-5-nitrobenzaldehyde and 30 ml of methanol were mixed, and the mixture was stirred at 80° C. for 1 hour. Thereafter, the mixture was cooled to 20° C. and the deposited crystals were collected by filtration. The collected crystals were washed with methanol and dried to give 3.22 g of (R)-N-(5-nitrosalicylidene)-2-amino-1,1-diphenyl-1-propanol. Yield 97.2%

$^1$H-NMR (CDCl$_3$, TMS, ppm) δ: 1.29 (d, 3H, J=6.6 Hz), 2.61 (s, 1H), 4.65 (q,1H,J=6.6 Hz), 6.82–6.89 (m,1H), 7.20–7.54 (m, 10H), 8.12–8.15 (m, 2H), 8.26 (s, 1H)

Elemental analysis Found: C, 70.1%; H, 5.4%; N, 7.4%. Calcd: C, 70.2%; H, 5.3%; N, 7.5%.

Example 5

66.12 g of 2,5-dimethyl-2,4-hexadiene and 4 μg of phenylhydrazine were added to a 100 ml Schlenk tube purged with a nitrogen gas having the oxygen concentration of 1%, and the mixture was stirred at 80° C. for 30 minutes. Thereafter, a toluene solution of a copper complex catalyst prepared from 3.59 mg of copper acetate monohydrate and 8.73 mg of (R)-N-(5-nitrosalicylidene(2-amino-1,1-di(2-methoxyphenyl)-1-propanol, and a 93.9 g of a 2,5-dimethyl-2,4-hexadiene solution containing 2.28 g of ethyl diazoacetate were added dropwise at the same temperature over 2 hours, respectively. Thereafter, the mixture was further stirred and kept at the same temperature for 30 minutes, the resulting reaction mixture was analyzed by gas chromatography, which revealed that the yield of ethyl 2,2-dimethyl-3-(2-methyl-1propenyl)cyclopropanecarboxylate was 93.5% and a trans/cis ratio was 59/41. The optical purity of (+)-trans-isomer was 56% e.e. and 49% e.e. for a cis compound.

Comparative Example 2

Ethyl 2,2-dimethyl-3-(2-methyl-1-propenyl)cyclopropanecarboxylate was produced according to a similar manner as that of Example 5 except that 7.83 mg of N-salicylidene-2-amino-1,1-di(2-methoxyphenyl)-1-propanol was used instead of 8.73 mg of N-(5-nitrosalicylidene)-2-amino-1,1-di(2-methoxyphenyl)-1-propanol. The yield was 89.3% and a trans/cis ratio was 60/40. The optical purity of (+)-trans-isomer was 34% ee and the optical purity of (+)-cis-isomer was 35% ee.

Example 6

Ethyl 2,2-dimethyl-3-(2-methyl-1-propenyl)cyclopropanecarboxylate was produced according to a similar manner as that of Example 5 except that the reaction was performed in the presence of 0.066 g of cumene hydroperoxide which is an oxydizing agent and a 100 ml Schlenk tube purged with a nitrogen gas in Example 5. The yield was 95.8%, and trans/cis ratio was 58/42. The optical purity of (+)-trans-isomer was 61% ee and that of (+)-cis-isomer was 53% ee.

Comparative Example 3

Ethyl 2,2-dimethyl-3-(2-methyl-1-propenyl)cyclopropanecarboxylate was produced according to a similar manner as that of Comparative Example 2 except that the reaction was performed in the presence of 0.066 g of cumene hydroperoxide which is an oxydizing agent and a 100 ml Schlenk tube purged with a nitrogen gas in Comparative Example 2. The yield was 94.2% and a trans/cis ratio was 60/40. The optical purity of a (+)-trans-isomer was 36% e.e. and that of (+)-cis-isomer was 36% e.e.

Example 7

Ethyl 2,2-dimethyl-3-(2-methyl-1-propenyl)cyclopropanecarboxylate was produced according to a similar manner as that of Example 6 except that an amount of cumene hydroperoxide to be used was 0.26 g in Example 6, The yield was 81.1% and a trans/cis ratio was 59/41. The optical purity of (+)-trans-isomer was 46% e.e. and that of (+)-cis-isomer was 38% e.e.

Comparative Example 4

Ethyl 2,2-dimethyl-3-(2-methyl-1-propenyl)cyclopropanecarboxylate was produced according to a similar manner as that of Comparative Example 3 except that an amount of cumene hydroperoxide to be used was 0.26 g in Comparative Example 3. The yield was 8.5% and a trans/cis ratio was 59/41. The optical purity of (+)-trans-isomer was 21% e.e. and that of (+)-cis-isomer was 20% e.e.

Example 8

Ethyl 2,2-dimethyl-3-(2-methyl-1-propenyl)cyclopropanecarboxylate was obtained in a similar manner as in Example 2 except that 5.22 mg of (R)-N-(3,5-dichlorosalicylidene)-2-amino-1,1-di(2-methoxyphenyl)-1-propanol was used instead of (R)-N-(5-nitrosalicylidene)-2-amino 1,1-di(2-methoxyphenyl)-1-propanol. The yield was 94.2% and a trans/cis ratio was 60/40. The optical purity of (+)-trans-isomer was 65% e.e. and that of (+)-cis-isomer was 60% e.e.

Example 9

66.12 g of 2,5-dimethyl-2,4-hexadiene and 4 μg of phenylhydrazine were added to a 100 ml Schlenk tube purged with nitrogen, a toluene solution of a copper complex catalyst prepared from 22.9 mg of a copper naphthenate/toluene solution containing 5% by weight of copper metal copper and 7.53 mg of N-(5-nitrosalicylidene)-2-amino-1,1-diphenyl-1-propanol, and 9.9 g of a 2,5-dimethyl-2,4-hexadiene solution containing 2.28 g of ethyl diazoacetate were added dropwise at 80° C. over 2 hours, respectively. Thereafter, the mixture was stirred and kept at the same temperature for 30 minutes, the resulting reaction mixture was analyzed by gas chromatography. The yield of ethyl 2,2-dimethyl-3-(2-methyl-1-propenyl)cyclopropane-carboxylate was 96.3% and a trans/cis ratio was 61/39. The optical purity analyzed by liquid chromatography was 52% e.e. for (+)-trans-isomer and 44% e.e. for (+)-cis-isomer.

Example 10

3.8 g of (R)-2-amino-1,1-di(2-methoxyphenyl)-1-propanol, 2.0 g of 2-hydroxy-3-fluorobenzaldehyde and 22 g of toluene were mixed and warmed to 80° C. and stirred at the temperature for 1 hr. Solvent was evaporated to give crystals. After 12 g of toluene were added thereto and warmed to dissolve the crystals at 80° C., 6 g of heptane were added thereto and cooled to a room temperature. Deposited crystals were collected by filtration, and washed with a mixed solvent of 3 g of toluene and 1.5 g of heptane, dried to give 4.37 g of (R)-N-(3-fluorosalycylidene)-2-amino-1,1-di(2-methoxyphenyl)-1-propanol as yellowish powder. Yield: 80.7%. Mp.116~118° C.

$^1$H-NMR (CDCl$_3$, TMS, ppm) δ: 1.34 (d, 3H), 3.56(d, 6H), 5.14(q, 1H), 5.49(s, 1H), 6.47–7.26(m, 9H), 7.56–7.68 (m, 2H), 8.16(s, 1H).

Example 11

0.97 g of (R)-2-amino-1,1-di(2-n-butoxy-5-tert-butylphenyl)-1-propanol, and 0.33 g of 2-hydroxy-5-nitrobenzaldehyde were dissolved in a mixed solvent of 20 ml of ethanol and 20 ml of toluene, and refluxed for 1 hr, and the reaction mixture was evaporated to give 1.2 g of (R)-N-(5-nitrosalycylidene)-2-amino-1,1-di(2-n-butoxy-5-tert-butylphenyl)-1-propanol as yellowish powder.

Yield: 94.9%. Mp. 67.9° C. $[α]_{546}$–308° (c=0.1% Chloroform).

$^1$H-NMR (CDCl$_3$, TMS, ppm) δ: 0.87–0.93(m, 6H), 1.15 (s, 9H), 1.29–1.31(m, 4H), 1.33(s, 9H), 1.36(s, 3H), 1.46–1.56(m, 4H), 3.72–3.85(m, 4H), 6.63–8.05(m, 9H), 8.57(s, 1H).

Elemental analysis Found: C, 71.5%; H, 8.1%; N, 4.6%. Calcd: C, 72.2%; H, 8.2%; N, 4.4%.

Example 12

Ethyl 2,2-dimethyl-3-(2-methyl-1-propenyl)cyclopropanecarboxylate was obtained in a similar manner as in Example 5 except that 9.2 mg of (R)-N-(3,5-dichlorosalycyliden)-2-amino-1,1-di(2-methoxyphenyl)-1-propanol was used in place of 8.73 mg of (R)-N-(5-nitrosalycyliden)-2-amino-1,1-di(methoxyphenyl)-1-propanol.

Yield 94.4%, Trans/cis ratio: 60/40, Optical purity of the trans-isomer: 58% e.e., Optical purity of cis-isomer: 53% e.e.

Example 13

Ethyl 2,2-dimethyl-3-(2-methyl-1-propenyl)cyclopropane-carboxylate was obtained in a similar manner as in Example 5 except that 8.19 mg of (R)-N-(3-fluorosalycyliden)-2-amino-1,1-di(2-methoxyphenyl)-1-propanol was used in place of 8.73 mg of (R)-N-(5-nitrosalycyliden)-2-amino-1,1-di(methoxyphenyl)-1-propanol.

Yield 93.6%, Trans/Cis ratio: 60/40, Optical purity of the trans-isomer: 46% e.e., Optical purity of Cis-isomer: 43% e.e.

Example 14

Ethyl 2,2-dimethyl-3-(2-methyl-1-propenyl)cyclopropane-carboxylate was obtained in a similar manner as in Example 7 except that 12.6 mg of (R)-N-(5-nitrosalycyliden)-2-amino-1,1-di(5-tert-butyl-2-n-butoxyphenyl)-1-propanol was used in place of 8.73 mg of (R)-N-(5-nitrosalycyliden)-2-amino-1,1-di(methoxyphenyl)-1-propanol.

Yield 91.3%, Trans/cis ratio: 56/44, Optical purity of the trans-isomer: 51% e.e. Optical purity of cis-isomer: 35% e.e.

Example 15

0.52 g of (R)-N-(5-nitrosalycylidene)-2-amino-1,1-di(5-tert-butyl-2-n-butoxyphenyl)-1-propanol prepared in Example 11, 0.164 g of copper acetate monohydrate and 40 ml of toluene were charged in a 100 ml glass flask, and the resulting mixture was reacted at 80° C. for 1 hr. After cooled to a room temperature, the reaction solution was transferred to a separatory funnel and thoroughly mixed with 30 ml of an aqueous sodium hydroxide solution, then settled and separated. Separated layer was washed twice with deionized water and separated organic phase was evaporated to give 0.53 g of copper complex as green powder.

Decomposition Temp: 110–130° C. $[α]_{546}$+314° (c=0.1% chloroform)

Elemental Analysis Found: C, 66.9%; H, 7.4%; N, 3.8%; Cu, 7.66%.

Example 16

6.9 mg of the copper complex prepared in Example 15, 10 ml of ethyl acetate and 1.1 mg of phenylhydrazine were charged in a 50 ml Schlenk glass tube reactor purged with nitrogen gas equipped with a magnetic stirrer to give a catalyst solution. 5 ml of the catalyst solution and 3.5 g of isobutylene were charged in a 100 ml stainless steel autoclave purged with nitrogen gas, and to the resulting solution was added 10 ml toluene solution containing ethyl diazoacetate, of which content is 20 mmol, at 40° C. for 2 hrs. After stirring at the same temperature for 30 min, the reaction solution was cooled. Content of ethyl 2,2-dimethyl-3-(2-methyl-1-propenyl)cyclopropanecarboxylate was analyzed by gas-chromatography analysis.

Yield: 91%.

After hydrolysis of the obtained ester, the acid was derivatized to its 1-menthyl ester and the optical purity was measured to show 87% e.e.

Example 17

9.8 g of (R)-N-(5-nitrosalicylidene)-2-amino-1,1-di(2-methoxyphenyl)-1-propanol, 4.0 g of copper acetate monohydrate, and 550 g of toluene were charged in a 100 ml glass flask and reacted at 80° C. for 1 hr. After being cooled to a room temperature, 8.7 g of 28 (wt) % sodium methylate were added thereto and stirred for 10 min. Then the reaction mixture was mixed with 200 g of water and separated by a separatory funnel. Separated oil layer was evaporated to give 11.2 g of copper complex as green powder.

Decomposition Temp: 158~165° C. $[α]_{546}$+927° (c=0.1%, Chloroform)

Elemental Analysis Found: C, 60.1%; H, 4.9%; N, 5.2%; Cu, 10.4%.

Example 18

0.5 g of the copper complex obtained in Example 17, 100 g of 2,5-dimethyl-2,4-hexadiene were charged in a 100 ml glass flask, and reacted at 80° C. for 1 hr under stirring. A green solid was precipitated on cooling the reaction mixture. Precipitated crystals were collected by filtration and dried to give 0.4 g of an adduct as green powder.

Elemental Analysis Found: C, 61.1%; H, 5.3%; N, 5.0%; Cu, 11.7%. Calcd: C, 60.8%; H, 5.3%; N, 5.1%; Cu, 11.5%.

(Calcd as an adduct of two molecules of a copper complex and one molecule of 2,5-dimethyl-2,4-hexadiene)

Example 19

5.53 mg of the adduct obtained in Example 18, 66.1 g of 2,6-dimethyl-2,4-hexadiene, and 4 μg of phenylhydrazine were charged in a Schlenk tube purged with nitrogen gas, to the resulting mixture was dropwise added a 9.9 g of a solution of 2,5-dimethyl-2,4-hexadiene solution containing 2.3 g of ethyl diazoacetate over 2 hrs and kept at the same temperature for 30 min under stirring. The resulting reaction mixture was analyzed by gas-chromatography analysis. 2,2-dimethyl-3-(2-methyl-1-propenyl)cyclopropane-carboxylate was obtained in 97.2% yield. Trans/cis ratio was 58/42. Optical purities of the trans-isomer and cis-isomer were 62.5% e.e. and 53.2% e.e.

Example 20

19.6 g (44.9 mmol) of (R)-N-(5-nitrosalicylidene)-2-amino-1,1-di(2-methoxyphenyl)-1-propanol, 8.96 g (44.9 mmol) of cupric acetate, and 160 g of toluene were mixed in a flask and reacted at 80° C. for 1 hr under stirring. The reaction solution was cooled to 10° C. and blue-green chrystalls were deposited. Deposited crystals were collected by filtration, washed with 50 g of cold toluene, and dried at room temperature to give 19.1 g of a copper complex of (R) N-(5-nitrosalicylidene)-2-amino-1,1-di(2-methoxyphenyl)-1-propanol in a yield of 82.0%.

Example 21

19.6 g (44.9 mmol) of (R)-N-(5-nitrosalicylidene)-2-amino-1,1-di(2-methoxyphenyl)-1-propanol, 8.96 g (44.9 mmol) of cupric acetate, and 160 g of toluene were mixed in a flask and reacted at 80° C. for 1 hr under stirring. 100 g of n-heptane were added to the reaction solution to precipitate blue-green chrystals. The precipitated reaction mixture was cooled to 10° C. and filtered to collect the crystals. Collected crystals were washed with 100 g of n-heptane, and dried at room temperature to give 22.1 g of a copper complex of (R) N-(5-nitro-salicylidene)-2amino-1,1-di(2-methoxyphenyl)-1-propanol in a yield of 99.0%.

Example 22

0.46 of a copper complex of (R)-N-(3,5-dichlorosalicylidene)-2-amino-1,1-di(2-methoxyphenyl)-1-propanol was obtained in a yield of 97.9% according to a similar manner as in Example 21 except that 0.415 g (0.901 mmol) of (R)-N-(3,5-dichlorosalicylidene)-2-amino-1,1-di(2-methoxyphenyl)-1-propanol was used in place of (R)-N-(5-nitrosalicylidene)-2-amino-1,1-di(2-methoxyphenyl)-1-propanol and 0.180 g (0.901 mmol) of cupric acetate, 10 g of toluene, 10 g of n-heptane for precipitation of the crystals, 10 g of n-heptane for washing the crystals were used.

Example 23

0.434 of a copper complex of (R)-N-(5-nitrosalicylidene)-2-amino-1,1-diphenyl-1-propanol was obtained in a yield of 99.1% according to a similar manner as in Example 21 except that 0.376 g (1.00 mmol) of (R)-N-(5-nitrosalicylidene)-2-amino-1,1-diphenyl-1-propanol was used in place of (R)-N-(5-nitrosalicylidene)-2-amino-1,1-di(2-methoxyphenyl-1-propanol and 0.20 g (1.0 mmol) of cupric acetate, 10 g of toluene, 10 g of n-heptane as a poor solubility solvent, 10 g of n-heptane for washing the crystals were used.

Example 24

33.06 g (300 mmol) of 2,5-dimethyl-2,4-hexadiene, 4.97 mg (0.01 mmol) of a copper complex of (R)-N-(5-nitrosalicylidene)-2-amino-1,1-di(2-methoxyphenyl)-1-propanol were charged in a 100 ml Schlenk tube purged with nitrogen gas and 4 µg of phenylhydrazine was added thereto. 1.14 g (10 mmol) of ethyl diazoacetate was added the resulting solution over 2 hrs and stirred at the same temperature for 30 min. The gas chromatography analysis of the reaction solution showed that the yield of chrysanthemate was 97.6%, trans/cis ratio was 58/42. High-performance liquid chromatography analysis showed that optical purity of the trans-isomer was 63% e.e and cis-isomer was 57% e.e.

Example 25

Chrysanthemate was produced in a similar manner as in Example 24 in a yield of 97.6%, where trans-cis ratio was 60/40, trans-isomer was 61% e.e and cisisomer was 56% e.e. except that 5.22 mg (0.01 mmol) of a copper complex of (R)-N-(3,5-dichlorosalicylidene)-2-amino-1,1-di(2-methoxypheny)-1-propanol was used in place of 4.97 mg of a copper complex of (R)-N-(5-nitrosalicylidene)-2-amino-1,1-di(2-methoxyphenyl)-1-propanol.

Comparative Example 5

1.0 g (2.56 mmol) of (R)-N-(salicylidene)-2-amino-1,1-diphenyl-propanol and 0.511 g (2.56 mmol) of cupric acetate were mixed in 5 g of toluene and reacted at 80° C. for 1 hr under stirring. Then 50 g of n-heptane was added thereto and cooled to 10° C., which produced no precipitated product and remain as a clear solution.

What is claimed is:
1. An optically active salicylideneaminoalcohol compound of formula (1):

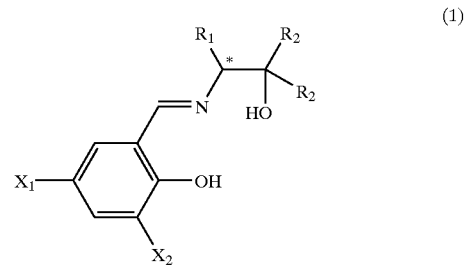

wherein
R$_1$ represents an alkyl group which may be substituted with a group selected from an alkoxy group, an aralkyloxy group, an aryloxy group and cycloalkoxy group, an aralkyl, aryl or cycloalkyl group all of which may be substituted with a group selected from an alkyl group, an alkoxy group, an aralkyloxy group, an aryloxy group and a cycloalkoxy group, R$_2$ represents an alkyl group, a cycloalkyl group, or an aralkyl or phenyl group which may be substituted with a group selected from an alkyl group, an alkoxy group, an aralkyloxy group, an aryloxy group and a cycloalkoxy group, when X$_1$ represents a nitro group, X$_2$ is a hydrogen atom, when X$_1$ represents a chlorine atom, X$_2$ is a chlorine atom, and when X$_1$ is a hydrogen atom, X$_2$ is a fluorine atom; and the carbon atom denoted by "*" is an asymmetric carbon atom having either an S or R configuration.

2. An optically active salicylideneaminoalcohol compound according to claim 1, wherein R$_1$ and R$_2$ are the same or different and independently represent an alkyl group, an aralkyl group, a phenyl group, a 2-methoxyphenyl group, a 2-tert-butoxy-5-tert-butylphenyl group or a 2-octyloxy-5-tert-butylphenyl group.

3. A process for producing an optically active salicylideneaminoalcohol compound as defined in claim 1, which comprises reacting an optically active amino alcohol of formula (2):

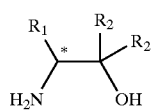
(2)

wherein $R_1$ represents an alkyl group which may be substituted with a group selected from an alkoxy group, an aralkyloxy group, an aryloxy group and cycloalkoxy group, an aralkyl, aryl or cycloalkyl group all of which may be substituted with a group selected from an alkyl group, an alkoxy group, an aralkyloxy group, an aryloxy group, and a cycloalkoxy group, $R_2$ represents a hydrogen atom, an alkyl group, a cycloalkyl group or an aralkyl or phenyl group which may be substituted with a group selected from an alkyl group, an alkoxy group, an aralkyloxy group, an aryloxy group and a cycloalkoxy group, and the carbon atom denoted by "*" is an asymmetric carbon atom having either an S or R configuration, with a 2-hydroxybenzaldehyde derivative of formula (3):

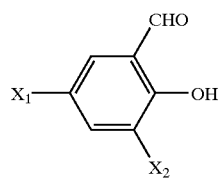
(3)

wherein when $X_1$ represents a nitro, $X_2$ is a hydrogen atom, when $X_1$ represents a chlorine atom, $X_2$ is a chlorine atom, and when $X_1$ is a hydrogen atom, $X_2$ is a fluorine atom.

4. A process according to claim 3, wherein $R_1$ and $R_2$ are the same or different and independently represent an alkyl group, an aralkyl group, a phenyl group, a 2-methoxyphenyl group, a 2-tert-butoxy-5-tert-butylphenyl group or a 2-octyloxy-5-tert-butylphenyl group.

5. A chiral copper complex obtained by contacting a mono-valent or di-valent copper compound with an optically active salicylideneaminoalcohol compound as defined in claim 1 or 2.

6. An adduct comprising a chiral copper complex as defined in claim 5 and a prochiral olefin of formula (5):

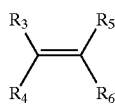
(5)

wherein $R_3$, $R_4$, $R_5$ and $R_6$ independently represent a hydrogen atom, a halogen atom, a (C1–C10)alkyl group which may be substituted with a halogen atom or a lower alkoxy group, a (C4–C8)cycloalkyl group, an aryl group which may be substituted with a halogen atom or a lower alkoxy group, or an alkoxy group; or $R_3$ and $R_4$, or $R_5$ and $R_6$ together form a cycloalkylene group having 2–4 carbon atoms, provided that one of $R_3$, $R_4$, $R_5$ and $R_6$ groups represents an alkenyl group which may be substituted with a halogen atom, an alkoxy group or an alkoxy carbonyl group, of which alkoxy may be substituted with a halogen atom or atoms, and provided that when $R_3$ and $R_5$ are the same, $R_4$ and $R_6$ are not the same.

7. A method for producing a chiral copper complex of formula (1)':

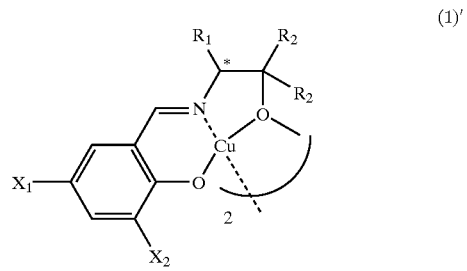
(1)' wherein $R_1$ and $R_2$ are the same or different and independently represent an alkyl group, an aralkyl group, a phenyl group, a 2-methoxyphenyl group, a 2-tert-butoxy-5-tert-butylphenyl group, or a 2-octyloxy-5-tert-butylphenyl group, when $X_1$ represents a nitro group, $X_2$ is a hydrogen atom, when $X_1$ represents a chlorine atom, $X_2$ is a chlorine atom, and when $X_1$ represents a hydrogen atom, $X_2$ is a fluorine atom, the carbon atom denoted by "*" is an asymmetric carbon atom having either an S or R configuration, which comprises contacting a di-valent copper compound, in an inert organic solvent, with a chiral salicylideneaminoalcohol compound of formula (1):

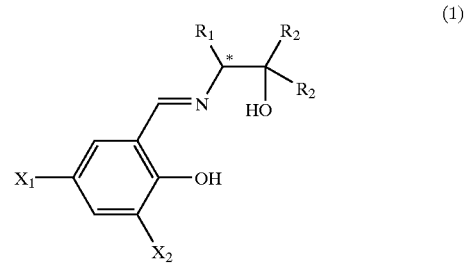
(1)

wherein $R_1$, $R_2$ $X_1$, $X_2$ and "*" respectively have the same meaning as defined above.

8. A method according to claim 7, which further comprises subjecting the resulting solution to precipitation and collecting the precipitated crystals of said chiral copper complex of formula (1)'.

9. A method according to claim 8, said precipitation is carried out by cooling the reaction solution or by adding an aliphatic hydrocarbon solvent.

* * * * *